United States Patent [19]
Chiu et al.

[11] Patent Number: 5,194,284
[45] Date of Patent: Mar. 16, 1993

[54] FOODS OPACIFIED WITH DEBRANCHED STARCH

[75] Inventors: Chung-Wai Chiu, Westfield; Matthew Henley, Somerset, both of N.J.

[73] Assignee: National Starch and Chemical Investment Holding Corporation, Wilmington, Del.

[21] Appl. No.: 837,443

[22] Filed: Feb. 14, 1992

Related U.S. Application Data

[63] Continuation-in-part of Ser. No. 350,057, May 10, 1989, Pat. No. 5,089,171, which is a continuation-in-part of Ser. No. 258,231, Oct. 14, 1988, Pat. No. 4,971,723.

[51] Int. Cl.$^5$ ................... A23L 1/0522; A23L 1/307
[52] U.S. Cl. .................................... 426/589; 426/613; 426/658; 426/804
[58] Field of Search ............... 426/804, 661, 658, 589, 426/578, 613

[56] References Cited

U.S. PATENT DOCUMENTS

| | | | |
|---|---|---|---|
| 3,532,602 | 10/1970 | Seidman et al. | 435/98 |
| 3,556,942 | 1/1971 | Hathaway | 435/210 |
| 3,565,765 | 2/1971 | Heady et al. | 195/31 |
| 3,632,475 | 1/1972 | Sugimoto et al. | 435/210 |
| 3,658,552 | 4/1972 | Carlson et al. | 99/78 |
| 3,666,557 | 5/1972 | Jensen et al. | 252/315.2 |
| 3,729,380 | 4/1973 | Sugimoto et al. | 195/31 R |
| 3,730,840 | 5/1973 | Sugimoto et al. | 195/31 R |
| 3,766,011 | 10/1973 | Kurimoto et al. | 435/98 |
| 3,879,212 | 4/1975 | Yoshida | 106/213 |
| 3,881,991 | 5/1975 | Kurimoto et al. | 195/31 R |
| 3,922,196 | 11/1975 | Leach et al. | 195/31 R |
| 3,956,519 | 5/1976 | Evans et al. | 426/564 |
| 3,959,510 | 5/1976 | Felton et al. | 426/590 |
| 3,962,465 | 6/1976 | Richter et al. | 426/48 |
| 4,001,435 | 1/1977 | Hirao et al. | 426/3 |
| 4,113,509 | 9/1978 | Leach et al. | 127/29 |
| 4,187,326 | 2/1980 | Serafino et al. | 426/590 |
| 4,211,842 | 7/1980 | Marshall | 435/210 |
| 4,221,609 | 9/1980 | Hughes | 127/29 |
| 4,279,940 | 7/1981 | Wurzburg et al. | 426/590 |
| 4,349,577 | 9/1982 | Tessler | 426/590 |
| 4,479,971 | 10/1984 | Eng et al. | 426/330 |
| 4,510,166 | 4/1985 | Lenchin et al. | 426/565 |
| 4,529,606 | 7/1985 | Fustier et al. | 426/330.3 |
| 4,529,613 | 7/1985 | Mezzino et al. | 426/590 |
| 4,560,651 | 12/1985 | Nielsen et al. | 435/95 |
| 4,619,833 | 10/1986 | Anderson | 426/548 |
| 4,705,691 | 11/1987 | Kupper et al. | 426/590 |
| 4,726,957 | 2/1988 | Lacourse et al. | 426/578 |
| 4,790,998 | 12/1988 | Swartz | 426/585 |
| 4,886,678 | 12/1989 | Chiu et al. | 426/578 |
| 4,911,946 | 3/1990 | Singer et al. | 426/658 |
| 4,937,091 | 6/1990 | Zallie et al. | 426/582 |
| 4,971,723 | 11/1990 | Chiu et al. | 252/315.3 |
| 4,971,828 | 11/1990 | Abbas et al. | 426/661 |
| 4,981,709 | 1/1991 | Furcsik et al. | 426/565 |
| 5,051,271 | 9/1991 | Iyengar et al. | 426/658 |
| 5,089,171 | 2/1992 | Chiu | 426/661 |
| 5,094,872 | 3/1992 | Furcsik et al. | |

FOREIGN PATENT DOCUMENTS

| | | |
|---|---|---|
| 0327288 | 8/1989 | European Pat. Off. |
| 89/09793 | 10/1989 | PCT Int'l Appl. |
| 89/12403 | 12/1989 | PCT Int'l Appl. |
| 1423780 | 2/1976 | United Kingdom |

OTHER PUBLICATIONS

Norman, B. E., "Debranching Enzymes in Dextrose Syrup Production", pp. 157-179 in *Maize, Recent Progress in Chemistry and Technology*, Academic Press, Inc., NY, NY (1982).

Slominska, L. et al., *Starch/Starke*, 11:386-390 (1985).

Rutenberg, M. W. "Starch and Its Modifications" pp. 22-36, in *Handbook of Water Soluble Gums and Resins*, Davidson, Editor, McGraw Hill, Inc., NY, NY (1980).

Willox, I. C., et al., *MBAA Technical Quarterly*, 14:105-110 (1977).

Harada, T., *Biotechnology and Genetic Engineering Reviews*, 1:39-63 (1977).

Manners, et al., "The Fine Structure of Amylopectin" in *Carbohydrate Research*, 90:99-110 (1981).

Anon, Annual Review 1989, Leatherhead Food R.A., p. 24.

Anon, *Bulletin-Leatherhead Food R.A.*, vol. 22 No. 6, Jun. 1988.

Anon., Fat Substitute Update, *Food Technology*, Mar. 1990, pp. 92-97.

Braudo, Von. E. E., et al., "Struktur und Eigenschaften von Maltodextrin Hydrogelen" *Starch/Starke*, 31:188-194 (1979).

*Primary Examiner*—Jeanette Hunter
*Attorney, Agent, or Firm*—Mary E. Porter; Edwin M. Szala

[57] ABSTRACT

This invention provides a method for opacifying a reduced-fat food, employing a partially or fully debranched starch. This starch is prepared by enzymatic hydrolysis of the alpha-1,6-D-glucosidic bonds of the starch, employing an endo-alpha-1,6-D-glucanohydrolase, such as pullulanase or isoamylase.

17 Claims, No Drawings

FOODS OPACIFIED WITH DEBRANCHED STARCH

This is a continuation-in-part of U.S. Ser. No. 350,057, filed May 10, 1989, now U.S. Pat. No. 5,089,171 issued Feb. 18, 1992, by Chiu which is a continuation-in-part of U.S. Ser. No. 258,231 filed Oct. 14, 1988, now U.S. Pat. No. -A-4,971,723 issued Nov. 20, 1990 to Chiu.

BACKGROUND OF THE INVENTION

This invention relates to a process for preparing stable opaque clouds in fluids, employing partially debranched starch as a clouding agent. This invention also relates a method for opacifying reduced-fat food employing partially or fully debranched starch.

As used herein, the term "opacity" refers to the amount of light transmittance of a solution or dispersion. As the solution or dispersion becomes cloudy, the opacity increases and the amount of light transmittance decreases. The solution or dispersion may be in liquid, solid or semi-solid form.

When the amount of fat in a food is reduced, many of the organoleptically desirable traits of the food's full-fat equivalent are surrendered to a degree proportionate to the amount of fat reduction, such desirable traits include mouthfeel, flavor richness and color or appearance. In particular, for foods having a creamy appearance (e.g., salad dressings) the removal of fat causes a loss of a desirable, opaque creamy color and appearance.

In the art of clouding fluids, especially in an attempt to achieve the desired opacity or cloud inherent in natural juices, it is known and standard practice to form oil-in-water emulsions using edible oils. In bottled beverages the cloud typically has been provided by citrus oils for citrus flavored beverages, or by neutral vegetable oils (e.g. coconut oil) for non-citrus flavored beverages. This cloud may be enhanced by the presence of weighing oils in the beverage. In dry beverage mixes the cloud has been provided by incorporating spray-dried emulsions containing plastic fats, such as hydrogenated coconut oil, cocoa butter (U.S. Pat. No. -A-4,529,606) or triglycerides (U.S. Pat. Nos. -A-4,705,691 and -A-4,790,998), or hydrogenated coconut oil, inorganic pigments such as titanium dioxide, and hydrocolloids such as gum Arabic (U.S. Pat. No. -A-3,658,522). Similar emulsions have been used in liquid beverage systems (U.S. Pat. No. -A-4,479,971).

A major drawback in the use of these clouds is the development of an undesirable soapy flavor which is due to oxidative rancidity and hydrolysis of the oil and fat. This problem is compounded because the soapy off-flavor develops during storage and may not be discovered until the product is sold. Development of this off-flavor in bottled and canned beverages may be due to factors such as heat and/or sunlight. In dry beverage mixes development of the off-flavor may be due to various factors, such as incomplete fixing of the fat initially, release of the fat during processing (due to the mechanical force and/or heat developed during ribbon blending), or adverse storage conditions (i.e., high heat and humidity). The presence of the fat leads to further problems such as clumping of the mix and insolubility of the mix when reconstituted in water. The use of the antioxidants to overcome the off-flavor problem is undesirable and often limited by government regulations. Hence, oil- and fat-free clouding agents have been explored.

Stable oil- and fat-free dry clouds have been described. One is a fat-free cloud prepared by co-drying and aqueous dispersion containing a major amount of a solubilized malto dextrin and a minor amount of xanthan gum and titanium dioxide (U.S. Pat. No. -A-4,187,326). Another involves the combination of a non-diary base and a new orange flavor emulsion to provide the cloud ("Breakfast Orange Drink Scores Formulation Breakthrough", *Processed Prepared Food*, June, 1980, p. 116). The non-diary base is a component of the stabilizer, which also contains pectin, carboxymethyl cellulose, xanthan gun and carrageenan gum. Typically non-dairy bases are stabilized dried emulsions containing 20 to 50% oil or fat.

Beverage cloud systems also have been prepared from protein-stabilized fat emulsions (U.S. Pat. No. -A-4,790,998) and starch-dispersions (U.S. Pat. No. -A-4,349,577). Other starch-containing (U.S. Pat. No. -A-4,529,613) and pectin-containing (U.S. Pat. No. -A-4,529,613) beverage clouds have been reported.

It is an object of this invention to provide a simple oil- and fat-free cloud and precloud which may be used in any fluids, especially in beverages and beverage mixes. It is a further object of this invention to provide a method for opacifying reduced-fat foods.

The use of starch as a fat-free clouding agent has met with less than optimal results due to the tendency of dilute starch dispersions to retrograde upon storage. The starch cloud is unstable because as the starch retrogrades, it tends to precipitate out of the fluid dispersion. In reduced-fat foods in semi-solid or solid form, or in reduced-fat foods formulated with one or more stabilizers, or in a beverage requiring only temporary opacity, starch retrogradation does not interfere with opacity.

Starch is a polysaccharide typically comprising a mixture of about 20–25% amylose and about 75–80% amylopectin which is organized into compact granular structures. Amylose is a linear polymer of D-anhydroglucose units which are linked by alpha-1,4-D-glucosidic bonds. Amylopectin is a large branched polymer of amylose chains linked by alpha-1,6-D-glucosidic bonds in a tree-like structure. Depending upon the variety of plant from which the starch is obtained, amylose ordinarily contains between 250 and 12,500 D-anhydroglucose units and amylopectin contains between 400,000 and 3,125,000 D-anhydroglucose units.

Enzymes, or mixtures of enzymes which saccharify and debranch starch, have been used in starch conversion processes for the commercial production of low molecular weight oligosaccharides and sugars, such as dextrose (glucose). Starch conversion is the degradation of starch to lower molecular weight components by treatment with acid, oxidizing agents, heat, alkali or alpha-amylase enzymes. Enzymatic conversion of starch typically involves the preferential hydrolysis of the alpha-1,4-D-glucosidic bonds by amylase, andonly limited, if any, hydrolysis of the alpha-1,6-D-glucosidic bonds.

In the enzymatic conversion of starch to thin-boiling (low viscosity) starch, hydrolysis of branched fragments may be incomplete. For sugar production, however, complete conversion of starch to sugar is desirable, and debranching enzymes have been used to degrade the branched alpha-limit dextrins (branched starch fragments which resist further hydrolysis by alpha-amylase) which remain intact after the enzymatic hydrolysis of alpha-1,4-D-glucosidic bonds. Glucoamylase, an enzyme which liquifies and saccharifies starch, has been employed for this purpose. Glucoamylase rapidly hydrolyzes alpha-1,4-D-glucosidic bonds and slowly hydrolyzes alpha-1,6-D-glucosidic bonds, releasing glucose. A debranching enzymes, such as pullulanase or isoamylase, which rapidly hydrolyzes only the alpha-1,6-D-glucosidic bonds, releasing short chain amylose, has been suggested for use in conjunction with glucoamylase and alpha-amylase to improve the efficiency of production of high dextrose syrups. These syrups are starting materials in the manufacture of crystalline dextrose and high fructose corn syrup. See Maize, *Recent Progress in Chemistry and Technology*, pp. 157–179, Academic Press, Inc. (1982); and Slominska, L., et al., Starch/Starke, 11:386–390 (1985).

Additionally, debranching enzymes (enzymes which release short chain amylose from starch) have been proposed for use in low calorie alcoholic beverage production to improve fermentability of branched starch fragments; in production of maltose from starch in conjunction with beta-amylase; in low DE maltodextrin (30–55 glucose units) production to induce proteins to aggregate in aqueous emulsions; and in enzymatic conversion of starch into a soluble syrup having a high quantity of disaccharides and trisaccharides. These debranching enzyme applications are directed to problems arising from the presence of branched starch or dextrin fragments following starch conversion processes. In each application, the debranching enzyme is employed in the complete conversion of starch to a variety of low molecular weight fragments such as sugars or maltodextrins. The thickening, adhesion and gelling characteristics of starch are lost.

The use of debranching enzymes to fully debranch starch, with hydrolysis of substantially all alpha-1,6-D-glucosidic bonds, so as to obtain pure, or amylopectin-free, low molecular weight amylose is taught in U.S. Pat. No. 3,730,840 to Sugimoto, et al; U.S. Pat. No. 3,881,991 to Kurimoto, et al; and U.S. Pat. No. 3,879,212 to Yoshida. These patents do not teach the conversion of starch to sugars and other soluble fragments. The object of these patents is to produce pure short chain amylose. The presence of any residual amylopectin is taught to be objectionable.

The background of enzyme-related starch technology does not suggest that useful starch compositions may be prepared by employing debranching enzymes to partially debranch the amylopectin component of the starch, yielding a mixture of short chain amylose, amylopectin and partially debranched amylopectin, with or without substantial conversion of the starch. The functional properties of the partially debranched starch of this invention are novel. Furthermore, nothing in the literature suggests the utility of an enzymatic process for partially debranching starch as a replacement, in whole, or in part, for oil- and fat-containing clouds which may be used in fluid dispersions. The enzymatic process offers significant advantages over other starch modification processes, particularly in food and cosmetic applications where the demand for "natural" products persists. Finally, nothing in the literature suggest that partially or fully debranched starch may be used to opacify a reduced-fat food, wherein the full-fat food equivalent for which the reduced-fat food is substituted contains an oil-in-water or a water-in-oil emulsion and is characterized by a creamy appearance.

SUMMARY OF THE INVENTION

This invention provides a process for preparing stable, opaque clouds in fluids, employing starches which are partially enzymatically debranched and which are more stable to precipitation in dilute dispersions than either native starches or fully debranched starches.

This invention further provides starches which are useful for forming stable opaque clouds in fluids and an enzymatic process for producing these starches, employing an alpha-1,6-D-glucanohydrolase, such as pullulanase, isoamylase or amylo-1,6-glucosidase.

The partially debranched starches comprise a mixture of partially debranched amylopectin, short chain amylose, and, optionally, amylopectin in proportions which are adjusted for particular applications by controlling the degree of debranching and the selection of starch source. Starches from several sources, such as corn, which contain long chain amylose, retain their long chain amylose content following enzyme treatment. Depending on the end use and the starch source selected, the starch may be debranched by treatment with an alpha-1,6-D-glucanohydrolase until up to 65%, by weight, of the starch has been debranched to short chain amylose.

This invention further provides a method for opacifying a reduced-fat food comprising the addition of a partially or a fully debranched starch to the food. Fully debranched high amylose starch is a preferred opacifier in heated foods.

The enzymatic treatment utilized in the process of this invention may be carried out on any pregelatinized starch which contains alpha-1,6-D-glucosidic bonds. In preparing the partially or fully debranched starch, the starch is selected from an appropriate source and slurried in water. The mixture is then cooked to gelatinize the starch. If desired, the starch may be used in granular form, but enzymatic degradation of granular starch proceeds slowly. The temperature and pH of the mixture are adjusted to the optimum for the particular enzyme to be used, and the slurry is then brought into contact with the enzyme.

The enzyme must be an endo-enzyme, capable of hydrolyzing the alpha-1,6-D-glucosidic linkages of the starch molecule, and incapable of any significant degree of hydrolysis of the alpha-1,4-D-glucosidic bonds. Because this endoenzyme is capable of hydrolyzing the 1,6-linkages of the starch molecule but incapable of hydrolyzing the 1,4-linkages, the residue of such a debranching procedure is a complex mixture which invariably contains a higher proportion of linear to branched chain molecules than the starting material. Thus, the composition and properties of partially debranched starches do not resemble those of converted starch products (i.e., thin-boiling starches, oligosaccharides, sugars and dextrins), nor those of fully debranched starch products (i.e., short and long chain amylose).

The enzyme is permitted to digest the starch until up to 65%, by weight, of the starch has been debranched to short chain amylose, or until the desired end point (i.e., sufficient debranching to provide stable opaque clouds in fluid dispersion) has been reached. Ordinarily the degradation will be carried out for periods ranging up to 24 hours, or more, depending on the temperature, enzyme and substrate concentrations, and other process variables. The enzyme degradation is then terminated by means of heat, chemical addition, or other methods known in the art for deactivating enzymes. The partially or fully debranched starch is permitted to "pre-retrograde" (i.e., age or temper) by cooling to room temperature, with agitation until the desired opacity is achieved. The partially or fully debranched starch composition may be spray dried, drum-dried or otherwise recovered in a form suitable for its intended use.

DESCRIPTION OF THE PREFERRED EMBODIMENTS

The starches which may be used in preparing the enzyme degraded starch herein may be derived from corn, tapioca, waxy maize, high amylose corn and other starches. As used herein "high amylose corn starch" refers to starch having at least 40% amylose that is obtained from hybrids of corn. Also included are the conversion products derived from any of the above starches, including fluidity or thin-boiling starches prepared by oxidation, alpha-amylase conversion, mild acid hydrolysis or heat dextrinization. Derivatized starches such as ethers and esters and other modified starches may also be employed.

The starch will preferably be a gelatinized starch (a precooked, cold-water-swelling starch) and also may be a fluidity starch converted by mild acid degradation, heat dextrinization, or any one of several methods that are well known in the art. See, e.g., M. W. Rutenberg, "Starch and Its Modifications" P. 22-36, in *Handbook of Water-Soluble Gums and Resins*, R. L. Davidson, editor, McGraw Hill, Inc., New York, N.Y., 1980. High amylose corn starch must be cooked at higher temperatures (e.g., 154° C.) than ordinary corn starch and at greater than atmospheric pressure (e.g., in a jet-cooker) to fully gelatinize the starch. If desired, the starch may be converted by treatment with an alpha-amylase to produce a fluidity starch in the manner disclosed in U.S. Pat. No. 4,726,957 to Lacourse, et al. A combination of one or more of these conversion techniques may be used. The conversion is typically carried out before derivatization or crosslinking, but may be carried out before or after the enzymatic treatment. Where a high viscosity debranched starch is desired, it is not desirable to convert the starch.

Where a low viscosity starch is desirable, a starch, such as waxy maize, which has been converted to a Water Fluidity (WF) of up to about 60 is preferred. Water Fluidity is an empirical measure of viscosity on a scale of 0-90, wherein fluidity is the reciprocal of viscosity.

If a converted starch is desired, enzymatic conversion employing alpha-amylase is a preferred method of conversion. The alpha-amylase conversion is carried out on a cooked starch dispersion until the desired viscosity is reached. The alpha-amylase is deactivated; the debranching enzyme is added to the starch dispersion; and debranching is carried out until the desired end point is reached. This two-step, enzymatic process is preferred because conversion and debranching may be carried out with a single cooking, filtering, and/or drying operation, other enzymes, such as beta-amylase, may be used in conjunction with these enzymes to further modify the starch.

For other products, derivatization to any degree of substitution or level of conversion that results in the desired viscosity and functional characteristics may be employed prior to, or following, enzymatic debranching. For example, if the debranched starch is employed as a beverage oil emulsifying agent, as well as a clouding agent, an octenylsuccinic derivative (OSA starch) is preferred. The starch is treated with octenylsuccinic acid anhydride to form a starch ester derivative containing from 0.25 to 3.0%, by weight, of octenylsuccinate.

In a preferred embodiment, the next step after preparing the starch derivative is to heat an aqueous dispersion of the derivatized starch to gelatinize the derivatized starch. The gelatinization process disrupts, in whole or in part, the associative bonding of the starch molecule within the raw starch granule, thereby making the molecule more accessible to the enzyme and permitting the enzyme to more easily and uniformly debranch the starch molecules. After a slurry of the starch has been gelatinized, the solids, temperature and pH of the dispersion are adjusted to provide optimum activity.

The optimum parameters for enzyme activity will vary depending upon the enzyme used. Thus, the rate of enzymatic debranching depends on factors including enzyme concentration, substrate concentration, pH, temperature, the presence or absence of inhibitors and other factors. Depending on the type of enzyme, or its source, various parameters may require adjustment to achieve optimum debranching rate. In general, enzymatic debranching is carried out at the highest feasible solids content to facilitate subsequent drying of the starch while maintaining optimum debranching rates. For example, for the pullulanase used herein to produce a starch suitable for use as a clouding agent, a precooked starch dispersion ranging up to 28% solids is preferred.

The practitioner will recognize that a higher solids starch system (e.g., above 50% solids) may be employed if the starch is gelatinized with a process which produces adequate mixing to uniformly blend the enzyme and the starch at higher solids. The practitioner will also recognize that the temperature, treatment time and other parameters of the enzymatic debranching process must be adjusted to the higher solids content. Processes which employ higher solids starch dispersions are intended to fall within the scope of this invention and may be used to prepare the modified starch herein.

Although the process of this invention is primarily illustrated by employing pullulanase (E.C. 2.3.1.41; pullulan 6-glucanohydrolase) as the enzyme component, other endo-alpha-1,6-glucanohydrolases, such as isoamylase (E.C. 3.2 1.68), or any other endo-enzyme which exhibits selectivity in cleaving the 1,6-linkages of the starch molecule, leaving the 1,4-linkages substantially intact and releasing short chain amylose, may be used to prepare the debranched starch herein.

In a preferred embodiment, the enzyme used is a heat stable pullulanase obtained from a novel species of Bacillus. This pullulanase will catalyze the hydrolysis of the alpha-1,6 linkages in pullulan and amylopectin, provided that there are at least two glucose units in the side chain. Pullulan is a linear polymer consisting essentially of D-glucopyranosyl triosenunits joined by alpha-1,6 linkages.

Optimum concentrations of enzyme and substrate are governed by the level of enzyme activity which will vary depending upon the enzyme source, the enzyme supplier and concentration of the enzyme provided in commercially available batches. Although the process of this invention makes use of an enzyme in solution, processes utilizing an enzyme immobilized on a solid support are intended to fall within the scope of this invention.

The reaction may proceed in the presence of buffers to ensure that the pH will be at the optimum level throughout the degradation. Buffers such as acetates, citrates, or the salts of other weak acids are acceptable. Other agents may be used to optimize enzyme activity. The reaction may be carried out in a pH range from about 3.0 to 7.5, with the preferred range being between 4.5 and 5.5, and the optimum being 5.0 when the temperature is 60° C. and the enzyme is the Bacillus pullulanase.

The aqueous starch dispersion should be held during the enzymatic debranching at a temperature of about 25°-100° C., the preferred range being 55°-65° C. and the optimum being at 60° C. at pH 5.0 for the Bacillus pullulanase. However, if shorter treatment times are desired, a temperature range from 60°-65° C. or a higher enzyme concentration may be used. Alternatively, a higher temperature may be employed if a thermally stable debranching enzyme which yields short chain amylose from starch is selected for use herein. As with other parameters of the enzyme reaction, the preferred and optimum temperature ranges will vary with changes in other parameters such as substrate concentration, pH and other factors affecting enzyme activity, and can be determined by the practitioner.

The enzymatic treatment is permitted to continue until the desired level of debranching is reached. The progress of the enzymatic treatment may be measured by various methods. If all critical parameters have been established for achieving a particular starch composition, then the treatment may be allowed to proceed to a predetermined relative end point in time. The end point may be determined by change in viscosity, by gel permeation chromatography, by reducing group content, iodine reaction or by any other method known in the art for measuring the degree of enzymatic debranching of the starch molecule.

In a preferred embodiment, the debranching end point is measured by determining the viscosity of a starch dispersion at 22° C. (72° F.) using the funnel viscosity method set forth in Example 1, below. The funnel viscosity method is a rapid, simple method for determining viscosity, in which the amount of time needed for a standard quantity of starch slurry to flow through a standard size funnel is recorded.

In a second preferred embodiment, the degree of starch debranching is measured by gel permeation chromatography. After separating the starch into its different molecular weight fractions, the percentage of short chain amylose is determined by calculating the percentage, by weight, of the low molecular weight fraction of the partially debranched starch. It will be understood by the practitioner that these percentages are approximately equal to the amount of short chain amylose which has been liberated from the amylopectin by the debranching enzyme. Experimental error in gel permeation chromatography (e.g., due to contamination by the enzyme, or by sugars or dextrins introduced with the starch, the enzyme solution, the buffer or other process components) may result in a percent low molecular weight fraction which may range up to 5% more than the percent short chain amylose of the starch sample.

The degree of starch debranching needed for a particular application depends on the type of starch utilized, the presence and nature of any substituent groups and degree, if any, of conversion. The practitioner will be able to select a suitable starch and determine the necessary debranching for any particular end-use with a minimum of experimentation.

For fully debranched starch, any starch may be employed. High amylose corn starch is preferred for opacifying reduced-fat food. If a 70% amylose corn starch is employed, the fully debranched product may contain up to 30% short chain amylose.

While any amylopectin-containing starch may be employed, the effects of partial enzymatic debranching will be more dramatic as the amylopectin content increases. Thus, waxy maize which contains about 100% amylopectin is preferred. Up to 65% of the waxy maize starch may be debranched to short chain amylose. The debranching of waxy maize starch should be controlled so that at least 35% partially debranched amylopectin remains.

In a preferred embodiment, waxy maize starch, or other waxy starch (e.g., waxy rice or barley starch), is partially debranched, yielding sufficient short chain amylose to form an opaque cloud in an aqueous starch dispersion. If a waxy maize starch is employed, the starch preferably comprises from 20 to 60% short chain amylose. For acid-converted waxy maize starch, debranching to yield from 30 to 50% short chain amylose is preferred.

After the desired degree of starch debranching has been reached, the enzyme is deactivated. Pullulanase is rapidly deactivated at temperatures above about 70° C., therefore, the reaction may be conveniently terminated by increasing the temperature of the starch dispersion to at least 75° C. for about 15 minutes.

After enzymatic hydrolysis is terminated, the partially or fully debranched starch dispersion is permitted to pre-retrograde by cooling to room temperature with agitation. This step may be accomplished by permitting the dispersion to age or temper for about 10 to 30 hours at about 20° to 30° C. with gentle agitation. This may also be accomplished by rapid cooling over a shorter time period (i.e., ½ to 10 hours) with agitation. This step improves the opacity and stability of the cloud formed by the partially debranched starch. For fully debranched starch, the pre-retrogradation step improves the starch's capacity for maintaining opacity in a reduced-fat food that is subjected to heat processing. This pre-retrogradation step may be followed by an additional 1 to 30 hour tempering treatment, without agitation, at 0° to 25° C. of the fully debranched starch dispersion prior to drying.

If the end-use application requires purification of the starch, the reaction impurities and by-products may be removed by dialysis, filtration, ion exchange processes, centrifugation or any other method known in the art for isolating and recovering the starch.

In reduced-fat foods, the partially or fully debranched starch may be used with a stabilizer at up to 5% by weight of the food to prevent precipitation of the starch and loss of opacity. The debranched starch/stabilizer combination is preferred in liquid reduced-fat foods. Suitable stabilizers include gums, and pregelatinized, fully dispersed, non-retrograded starches.

It is believed that the retrogradation of the fully debranched starch to form white, opaque, fine particles is responsible for providing superior opacity in foods containing such a starch in dispersed or suspended form. If the foods are heated to a degree sufficient to reverse starch retrogradation, the opacifying capacity of the starch is markedly reduced. Fully debranched high amylose corn starch is the preferred opacifier for heat-treated foods because this starch must be heated to very high temperature to reverse starch retrogradation and, therefore, remains opaque even during retort canning of food.

If a dried starch is desired for end use applications, the starch may be dehydrated by any method known in the art.

It is to be understood that the invention includes any starch blend which contains partially or fully debranched starch and is useful as a clouding agent. Thus, this invention includes blends of partially or fully debranched starch and other components, such as chemically modified starches, other polymers, flavoring oils and other clouding adjuncts, and includes multi-step processes in which an enzyme is employed in one step to partially or fully debranch starch. For example, this invention includes multi-step processes and starch blends wherein the starch is converted, derivatized, crosslinked or otherwise modified in addition to being subjected to enzymatic debranching.

The following examples will more fully illustrate the embodiments of this invention. In these examples, all parts and percentages are given by dry weight basis and all temperature are in degrees Celsius unless otherwise noted.

EXAMPLE 1

This example illustrates the preparation of representative partially debranched starches by the process of this invention.

The starches were converted, derivatized, or crosslinked, where applicable, prior to gelatinization and treatment with pullulanase. Except as provided elsewhere herein, to convert the starch, a slurry of 100 parts of starch in 150 parts of water was heated to 52° C., the indicated amount of hydrochloric acid (1.75%) was added, and the mixture was stirred for 16 hours at 52° C. The hydrolysis was stopped by neutralizing the mixture with alkali (a solution of 3% sodium hydroxide) to a pH of 5.5. The converted starch was recovered by filtration, washed and dried.

STARCH DEPRIVATION

To prepare the octenylsuccinic derivative, 100 parts of starch were slurried in 150 parts water, the pH was adjusted to 7.5 with sodium hydroxide, and the indicated amount of octenylsuccinic anhydride was added slowly while the pH was maintained at 7.5 with the alkali. The reaction was complete when no further addition of alkali was necessary. The pH was adjusted to between 4.0 and 6.5 and the resulting derivatives where recovered by filtration, washed and dried.

To prepare the acetate derivative, 100 parts of the starch was slurried in 150 parts water, adjusting the pH to 8.3 with 3% sodium hydroxide solution, and slowly adding the indicated amount of acetic anhydride while maintaining the pH at 8.3 with the above alkali. The reaction was complete when no further addition of alkali was necessary. The pH was adjusted to between 4.0 and 6.5 and the resulting derivative was recovered as above.

The crosslinked starch was prepared by slurrying 100 parts of the starch in 150 parts water, adding 0.8 part sodium hydroxide, 1.0 part sodium chloride, and then adding the indicated amount of phosphorus oxychloride. The slurry was agitated for 3 hours at room temperature. When the reaction was completed, the pH was adjusted to 5.5 with acid. The starch was recovered by filtration, washed and dried.

STARCH DEBRANCHING

An aqueous slurry (20-30% solids) was prepared employing the desired starch. The aqueous starch slurry was jet-cooked at approximately 149° C. (300° F.) to gelatinize the starch. The cooked starch dispersion was placed in a constant temperature bath at 58°-60° C. with constant stirring. The pH was adjusted to 5 with 3% hydrochloric acid.

Depending on the type of starch used and its amylopectin content, between 0.5 and 10.0 mls of pullulanase per 100 g of starch were added to the cooked starch dispersion. The pullulanase (E.C. 3.2.1 41, pullulan 6-glucano-hydrolase) which was used is produced by a novel species of Bacillus. This enzyme (Promozyme TM) was obtained from Novo Industri A/S of Denmark. The enzymatic activity of Promozyme in a 1.25 g/ml solution is standardized at 200 PUN/ml of solution. One PUN (Pullulanase Unit Novo) is the amount of enzyme which, under standard conditions, hydrolyzes pullulan, liberating reducing carbohydrate with a reducing power equivalent to 1 micro-mol glucose per minute. The procedure for determining PUN is available from Novo Industri A/S.

Thus, in the starch dispersion employing corn starch, 125 PUN of pullulanase per 100 g corn starch was added to the dispersion. For the waxy maize starch slurry (with higher amylopectin content), 750 PUN of pullulanase per 100 g waxy maize starch was added to the dispersion.

The amount of debranching was measured initially by the funnel viscosity test and subsequently by gel permeation chromatography.

WATER FLUIDITY MEASUREMENT

Water Fluidity (WF) is a measurement, on a scale of 0-90 WF, of the amount of conversion of a starch. It is inversely related to viscosity, i.e., as WF increases, viscosity decreases. A method for determining water fluidity is disclosed in U.S. Pat. No. -A-4,499,116, issued Feb. 12, 1985 to Zwiercan, et al.

FUNNEL VISCOSITY MEASUREMENT

To measure funnel viscosity at 19% solids, 38 g of the starch (anhydrous basis) was weighed into a tared 250 ml beaker (stainless steel) containing a thermometer and brought to 200 g total weight with distilled water. The sample was mixed to dissolve any lumps and heated or cooled to 22° C. (72° F.). A total of 100 ml of the cooked starch dispersion was measured into a graduated cylinder. It was then poured into a calibrated funnel while using a finger to close the orifice. A small amount was allowed to flow into the graduate to remove any trapped air, and the complete balance remaining in the graduate was poured back into the funnel. Using a timer, the time required for the 100 ml sample to flow through the apex of the funnel was recorded.

The funnel was a standard 58°, thick-wall, resistance glass funnel whose top diameter was about 9-10 cm with the inside diameter of the stem being about 0.381 cm. The funnel was calibrated so as to allow 100 ml of water to go through in 6 seconds using the above procedure.

CORN STARCH (CAUSTIC) FUNNEL VISCOSITY

Due to retrogradation of the starch which occurs when using corn starch, the funnel viscosity measurement was modified as follows for debranched corn starch:

1. the starch sample weight was reduced to 15 g (anhydrous basis);
2. sufficient hot (at least 90° C.) water was added to the starch to bring it to 150 g total weight;
3. 15 g of 25% w/v sodium hydroxide solution was added to the hot starch slurry; and
4. with stirring, the slurry was cooled 22° C. (72° F.) and the measurement carried out as set forth above.

GEL PERMEATION CHROMATOGRAPHY

Starches were prepared for analysis by slurrying 5 mg of starch in 4 ml of dimethylsulfoxide ("DMSO") containing 0.03M sodium nitrate and heating the slurry to 80° C. for at least 30 minutes to dissolve the starch. Samples (200 ul) were injected into an ALC/GPC-150C chromatograph (Waters Associates, Milford, Mass.) (equipped with a Nelson 3000 Series Chromatography Data System and two PLgel mixed 10 um columns (obtained from Polymer Laboratory, Amherst, Mass.), employing DMSO containing 0.03M sodium nitrate as the mobile phase) and eluted at a rate of 1 ml/min. The columns were calibrated using dextran standards (with molecular weights of 2,000; 20,000; 80,000; 500,000; and 2,000,000 obtained from Pharmacia Fine Chemicals, Piscataway, N.J.). The percentage short chain amylose was calculated from the relative area of the peak obtained within the molecular weight range from 500 to 20,000.

PREPARATION OF DEBRANCHED OSA WAXY MAIZE STARCHES

Employing the process set forth above, an OSA starch derivative was prepared by reacting 4,000 g of waxy maize starch with 1% octenylsuccinic anhydride. The starch was then jet cooked at pH 5.0 to yield a 23% starch dispersion. Pullulanase (80 mls) was added to the dispersion at 58° C. with agitation. After 24 hours, the funnel viscosity was 35 seconds at 19% solids and 22° C. (72° F.).

The debranching was continued by adding an additional 80 mls of pullulanase at 58° C. and agitating the dispersion for an additional 3 hours. The pullulanase was deactivated by heating the dispersion to about 80° C. The funnel viscosity was 12 seconds at 19% solids and 22° C. (72° F.). The starch dispersion was spray dried at an inlet temperature of 200°–210° C. and an outlet temperature of 80°–90° C. The spray-dried starch was screened through #40 mesh screen.

A second sample of OSA waxy maize starch (4,000 g) was prepared and debranched in the same manner as the first sample, except that 20 mls of pullulanase was employed in a single addition. Debranching continued for two hours at which time the funnel viscosity was 50 seconds at 10% solids and 22° C. (72° F.). This sample was spray-dried in the same manner as the first sample.

EXAMPLE 2

This example illustrates the preparation of partially debranched starch employing the enzyme isoamylase (glycogen 6-glucano-hydrolase; E.C. 3.2.1.68).

A cooked, 24% solids, aqueous dispersion of waxy maize starch (2,500 g) was treated with 5,000 units of a *Pseudomonas amyloderamosa* isoamylase (obtained from Sigma Chemical Company, St. Louis, Mo.). One unit of this isoamylase causes an increase in absorbance ($A_{610}$) of 0.1 in 1 hour using rice starch as a substrate.

The starch dispersion was heated to 45° C. at pH 4.0, the enzyme was added and the mixture was stirred for 26 hours. A portion of the mixture was removed, heated to 80° C. to deactivate the enzyme, and spray-dried and screened as in Example 1. The remaining portion of the starch mixture was enzymatically treated for a total of 43 hours, at which time the enzyme was deactivated and the starch dried and screened as above.

The quantity of short chain amylose obtained from isoamylase hydrolysis was measured with gel permeation chromatography. The 26 hour sample contained 21.9% and the 43 hour sample contained 28.4% short chain amylose.

EXAMPLE 3

This example illustrates the relationships between treatment time, funnel viscosity (or Water Fluidity) and percentage short chain amylose of the starches of this invention.

The partial enzymatic debranching process of Example 1 was carried out on the starches listed in Table I.

The funnel viscosity and percent short chain amylose were measured by the methods set forth above. Results are shown in Table I.

TABLE I

| Starch | Treatment Time (hrs.) | Funnel Viscosity (seconds) | % Solids | % Short Chain Amylose |
|---|---|---|---|---|
| Waxy-Maize Acid-Converted to 50 WF | | | | |
| 1 | 0.5 | 110 | 19 | 13.5 |
| 2 | 1.0 | 22 | 19 | 26.3 |
| 3 | 20.0 | 20 | 19 | 27.1 |
| 4 | 20.0 | 18 | 19 | 31.8 |
| 5 | 25.0 | 14 | 19 | 35.1 |
| 6 | 44.0 | 12 | 19 | 48.0 |
| Waxy-Maize | | | | |
| 1 | 0.25 | 110 | 19 | 22.1 |
| 2 | 1.0 | 52 | 19 | 23.8 |
| 3 | 20.0 | 20 | 19 | 32.6 |
| 4 | 20.0 | 16 | 19 | 40.0 |
| 5 | 24.0 | 12 | 19 | 45.6 |
| 6 | 45.0 | 12 | 19 | 51.9 |
| Corn[a] | | | | |
| 1 | 1.0 | 97 | 10 | 14.5 |
| 2 | 3.0 | 37 | 10 | 21.9 |
| 3 | 5.0 | 30 | 10 | 26.5 |
| 4 | 7.0 | 27 | 10 | 24.9 |
| 5 | 24.0 | 18 | 10 | 33.3 |
| 6 | 48.0 | 12 | 10 | 47.5 |

[a]Caustic Funnel Viscosity.

The results show generally that as reaction time increases, the percent short chain amylose increases and the funnel viscosity decreases in a non-linear fashion. Thus, one or more of these measurements may be employed to measure the progress of the enzymatic debranching.

EXAMPLE 4

This example illustrates the preferred mode for preparing partially debranched starches which are useful as opacifying agents.

Three starches were prepared for use herein. Tapioca and waxy maize starch samples were employed without further modification and a sample of waxy maize starch was acid-converted to 50 WF, using the method of Example 1. Gelatinized starch slurries were prepared as in Example 1.

A total of 30 mls of pullulanase per 100 g of starch, and 0.5 ml of pullulanase per 100 g of starch were added to different batches to achieve a funnel viscosity (at 19% solids and 22° C. (72° F.)) of 9-10 seconds and 18 seconds, respectively, after 18-22 hours of enzyme treatment of the waxy maize starches. The tapioca starch was debranched to a funnel viscosity of 56 seconds (at 19% solids and 22° C.) employing 0.2 mls of pullulanase per 100 g starch. Other tapioca starch samples were debranched to 76.2 seconds and 56.3 seconds (at 10% solids and 22° C.) employing 0.42 mls of pullulanase per 100 g of starch.

The debranching process was otherwise identical to that of Example 1, except that a pre-retrogradation step was employed prior to spray-drying.

In the pre-retrogradation step, partially debranched starch in the dispersed state was permitted to age to room temperature over a 24 hour period with gentle agitation. Before spray-drying by the method of Example 1, the starch dispersion was heated to a temperature of 55° C.

The utility of starches as stable opacifying agents was measured by the light transmittance method of Example 6. As shown in Table II, the pre-retrograded samples formed more opaque clouds, with excellent stability at a variety of treatment levels.

TABLE II

| STARCH | | OPACITY[C] % Transmittance | | | |
|---|---|---|---|---|---|
| Funnel Viscosity | % Starch | Initial | | 24 Hour | |
| (19% Solids) (22° C.) | Solids | A | B | A | B |
| Waxy Maize | 1.0 | 40.2 | 0.8 | 45.8 | 1.5 |
| 11.8 seconds | 0.5 | 62.1 | 1.5 | 67.1 | 2.2 |
| | 0.25 | 80.2 | 6.2 | 82.1 | 9.8 |
| | 0.1 | 87.3 | 27.6 | 88.0 | 33.1 |
| 16.5 seconds | 1.0 | 37.1 | 2.0 | 48.1 | 2.5 |
| | 0.75 | 44.1 | 3.2 | 48.7 | 3.7 |
| | 0.5 | 51.0 | 7.2 | 58.0 | 8.5 |
| | 0.25 | 68.2 | 21.0 | 76.1 | 25.7 |
| 50 WF Waxy maize | 1.0 | 35.0 | 0.8 | 47.0 | 1.5 |
| 11.3 seconds | 0.5 | 42.0 | 0.8 | 59.4 | 2.0 |
| | 0.25 | 61.0 | 2.1 | 68.2 | 7.0 |
| | 0.1 | 68.5 | 10.0 | 72.0 | 27.0 |
| 9.5 seconds | 1.0 | 9.2 | 1.2 | 18.4 | 3.7 |
| | 0.75 | 11.1 | 2.1 | 20.2 | 6.1 |
| | 0.5 | 28.5 | 5.8 | 36.6 | 9.5 |
| | 0.25 | 37.5 | 15.8 | 45.0 | 30.9 |
| Fully Debranched Waxy | 1.0 | 1.1 | 0.9 | 80.0 | 77.4 |
| Maize (Crystalline) | 0.75 | 1.8 | 1.4 | 70.2 | 81.0 |
| about 6 seconds[D] | 0.5 | 1.9 | 1.5 | 75.0 | 83.1 |

[A]No pre-retrogradation step.
[B]Pre-retrogradation step used.
[C]As the % transmittance increases, the opacity decreases. See Example 6.
[D]High % transmittance after 24 hours is probably due to starch settling out of the dispersion.

EXAMPLE 5

This example illustrates a preferred method for debranching converted starch, wherein the conversion and debranching processes are carried out in a two-step, enzymatic process.

A cooked dispersion of waxy maize starch (22% solids) was treated with alpha-amylase (72 KNU/kg starch) (obtained from Novo Industries, AS, Denmark, and sold under their trademark, Novo Ban 1200) at 85° C. and a pH of 5.0. One Kilo Novo alpha-amylase Unit (1 KNU) is the amount of enzyme which breaks down 5.26 g starch per hour in a Novo standard method employing soluble starch at 37° C. and PH 5.6, for 7-20 minutes in the presence of 0.0043M calcium. When the dispersion reached the desired viscosity (see Table III), the alpha-amylase was deactivated by heating to over 95° C. for 30 minutes.

The starch dispersion was cooled to 58° C. and treated with pullulanase (5,000 PU/kg starch). When the desired viscosity was reached (see Table III), the pullulanase was deactivated by heating to 80° C. for 30 minutes. The starch cloud was formed by permitting the dispersion to age by cooling to room temperature over a 24 hour period. The opacity of the starch cloud was measured by the light transmittance method of Example 6. Results are summarized in Table III.

TABLE III

| STARCH Viscosity[a] | OPACITY % Transmittance[b] | |
|---|---|---|
| Alpha-amylase/Pullulanase | Initial | 24 Hour |
| 200 seconds/12 seconds | 0.8 | 5.4 |
| 50 seconds/10 seconds | 1.5 | 29 |
| 11 seconds/9 seconds | 16 | 30 |

[a]Funnel Viscosity at 19% solids and 22° C.
[b]Measured at 0.5% solids.

EXAMPLE 6

This example illustrates that the starch of this invention may be used to form a stable, opaque cloud when dispersed in an aqueous medium.

Waxy maize starches and acid-converted (50WF) waxy maize starches were debranched by the method of Example 1 to the funnel viscosities listed in Table IV.

Additionally, a tapioca starch was debranched by the method of Example 1 to a funnel viscosity of 54 seconds (10% solids). The tapioca dispersion was passed through a hand homogenizer before measuring transmittance. For comparative purposes, fully debranched, crystalline short chain amylose, prepared by the method claimed in U.S. Pat. No. -A-3,730,840, was dispersed in distilled water at 1.0% solids and the transmittance of the dispersion was measured.

The percent light transmittance of a 1% solids starch dispersion in distilled water (0.2% solids for tapioca) was measured initially and after 24 hours using a Brinkman P.C. 800 colorimeter. Results are set forth in Table IV. As the cloud forming capacity of the starch improved, the percent light transmittance decreased. A significant increase in percent light transmittance after 24 hours indicates the starch cloud was not stable, or had settled out of the dispersion.

Waxy maize starches which had been debranched to yield 20 to 65% short chain amylose produced the most stable clouds. Fully debranched starch (U.S. Pat. No. -A-3,730,840) did not form a stable, opaque cloud.

TABLE IV

| Starch[a] | Funnel Viscosity (seconds) | % Solids | % Short Chain Amylose | % Transmittance[b] | |
|---|---|---|---|---|---|
| | | | | Initial | After 24 hrs. |
| Waxy Maize | | | | | |
| A | 96 | 10 | — | 20 | 23 |
| B | 27.6 | 10 | 13.5 | 22 | 25 |
| C | 13.0 | 19 | 40 | 3.0 | 10.4 |
| D | 11.7 | 19 | 45 | 0.8 | 1.5 |
| Acid-Converted (50 WF) | | | | | |
| E | 20.6 | 19 | 26.5 | 3.9 | 10.2 |
| F | 10.2 | 19 | 50 | 3.0 | 8.2 |
| G | 7.0 | 19 | over 60 | 0.9 | 77 |
| Tapioca | 54.0 | 10 | 13 | 9 | 23 |
| Fully Debranched (U.S. Pat. No. | — | — | 84 | 1 | 60 |

TABLE IV-continued

| Starch[a] | Funnel Viscosity (seconds) | % Solids | % Short Chain Amylose | % Transmittance[b] Initial | After 24 hrs. |
|---|---|---|---|---|---|
| -A-3,730,840) | | | | | |

[a]See Example 6.
[b]Some precipitate was observed in samples showing an increase in light transmittance after 24 hours.

EXAMPLE 7

This example illustrates the relative effectiveness of various partially debranched starches when employed as opacifying agents. A commercially available opacifying agent ("Borden 187 Cloud" a dried, starch encapsulated coconut fat, obtained from Borden, Inc., Anaheim, Calif.) was employed as a control. Samples of fully branched starches also were employed as controls.

Waxy maize, tapioca and 50WF acid-converted waxy maize starch were debranched as in Example 4, except that some samples (as indicated in Tables V, VI and VII) were prepared without the pre-retrogradation step. Aqueous starch clouds were prepared as in Example 5 except that one tapioca starch sample (see Table VII) was passed through a hand homogenizer twice before evaluation of the cloud. Additionally, samples of the 1% solid starch dispersions were diluted to 0.75%, 0.5%, 0.25% and 0.1% solids prior to evaluation. Transmittance was measured as in Example 6.

Results are reported in Tables V, VI and VII. The homogenation of tapioca starch dispersion improved cloud formation and stability in more highly debranched samples. All debranched tapioca starches formed opaque clouds at lower starch concentrations than the branched tapioca control.

The pre-retrograded, partially debranched waxy maize starch formed a more opaque cloud than starches prepared without the pre-retrogradation step.

The fully branched starch controls did not form effective clouds. Fully debranched starch did not form stable clouds.

The cloud formed by the pre-retrograded 50WF waxy maize starch at 0.25% solids was equivalent in opacity and stability to the cloud formed by encapsulated coconut fat at 0.1% solids. Thus, partially debranched waxy maize and tapioca starches are useful as opacifying agents.

TABLE V

| STARCH | Funnel Viscosity (Seconds) | % Starch Solids | OPACITY % Transmittance Initial | 24 Hour |
|---|---|---|---|---|
| Waxy maize | 96.0[a] | 1.00 | 19.6 | 23.2 |
| | | 0.75 | 26.3 | 29.3 |
| Waxy maize | 47.0[a] | 1.00 | 28.0 | 30.9 |
| | | 0.75 | 35.0 | 37.5 |
| Waxy maize | 34.1[a] | 1.00 | 29.0 | 31.6 |
| | | 0.75 | 34.7 | 37.9 |
| Waxy maize | 27.6[a] | 1.00 | 22.3 | 25.1 |
| | | 0.75 | 31.4 | 35.4 |
| Waxy maize | 20.6[a] | 1.00 | 24.1 | 28.2 |
| | | 0.75 | 32.9 | 37.6 |
| Waxy maize | 16.5[b] | 1.00 | 2.0 | 2.5 |
| | | 0.75 | 3.2 | 3.7 |
| | | 0.50 | 7.2 | 8.5 |
| Waxy maize | 13.0[b] | 1.00 | 3.3 | 10.4 |
| | | 0.75 | 5.6 | 21.3 |
| | | 0.50 | 11.2 | 32.3 |
| Waxy maize | 11.7[b] | 1.00 | 0.8 | 1.5 |
| | | 0.50 | 1.5 | 2.2 |

TABLE V-continued

| STARCH | Funnel Viscosity (Seconds) | % Starch Solids | OPACITY % Transmittance Initial | 24 Hour |
|---|---|---|---|---|
| | | 0.25 | 6.2 | 9.8 |
| Control Fully Debranched Waxy Maize (Crystalline) | about 6 seconds[b] | 1.00 | 0.8 | 53.0 |
| | | 0.75 | 0.9 | 56.0 |
| Control Fully Branched Waxy Maize | — | 1.00 | 50.1 | 56.0 |
| Control | | 0.25 | 0.8 | 1.0 |
| Encapsulated Coconut Fat | — | 0.10 | 2.0 | 5.2 |

[a]Funnel viscosity in seconds at 10% solids and 22° C.
[b]Funnel viscosity in seconds at 19% solids and 22° C.
[d]Borden 187 cloud.

TABLE VI

| STARCH | Funnel Viscosity (Seconds) | % Starch Solids | OPACITY % Transmittance Initial | 24 Hour |
|---|---|---|---|---|
| 50 WF | 20.6[b] | 1.00 | 3.9 | 10.2 |
| Waxy Maize | | 0.75 | 6.7 | 25.1 |
| 50 WF | 18.0[b] | 1.00 | 4.5 | 16.2 |
| Waxy Maize | | 0.75 | 6.4 | 21.5 |
| 50 WF | 10.2[b] | 1.00 | 3.0 | 8.2 |
| Waxy Maize | | 0.75 | 0.8 | 2.0 |
| 50 WF | 11.3[b,c] | 1.00 | 1.1 | 1.2 |
| Waxy Maize Pre-retrograded | | 0.75 | 0.8 | 2.0 |
| | | 0.50 | 0.8 | 1.5 |
| | | 0.25 | 2.1 | 7.0 |
| 50 WF | 10.1[b] | 1.00 | 2.4 | 8.2 |
| Waxy Maize | | 0.75 | 1.1 | 7.8 |
| | | 0.50 | 2.3 | 18.1 |
| 50 WF | 9.6[b] | 1.00 | 1.2 | 3.7 |
| Waxy Maize | | 0.75 | 2.1 | 6.1 |
| | | 0.50 | 5.6 | 9.5 |
| Control Fully debranched 50 WF Waxy Maize Crystalline | about 6[b] | 1.00 | 0.9 | 77.4 |
| | | 0.75 | 1.4 | 81.0 |
| Control Fully branched 50 WF Waxy Maize | — | 1.00 | 60.5 | 70.1 |
| Control Encapsulated Coconut Fat[d] | — | 0.10 | 2.0 | 5.2 |

[b]Funnel viscosity in seconds at 19% solids and 22° C.
[c]Pre-retrogradation step used.
[d]Borden 187 cloud.

TABLE VII

| STARCH | Funnel Viscosity (Seconds) | % Short Chain[e] Amylose | % Starch Solids | OPACITY % Transmittance Initial | 24 Hour |
|---|---|---|---|---|---|
| Tapioca | 76.2[b] | 3% | 0.75 | 5.1 | 10.7 |
| | | | 0.50 | 5.4 | 30.2 |
| | 76.2[b,d] | 3% | 0.50 | 7.0 | 10.0 |
| Tapioca | 56.3[b] | 10% | 0.75 | 6.5 | 21.0 |
| | | | 0.50 | 7.0 | 28.0 |
| Tapioca | 45.6[b] | 17% | 0.75 | 6.6 | 54.0 |
| | | | 0.50 | 6.7 | 63.0 |
| Tapioca | 22.6[b] | 21% | 0.75 | 8.8 | 54.0 |
| | | | 0.50 | 10.2 | 72.3 |
| Tapioca | 10.2[b] | 50% | 0.75 | 15.5 | 61.5 |
| | | | 0.50 | 18.1 | 75.0 |
| Tapioca | 54.0[b,d] | 13% | 0.50 | 1.8 | 9.0 |
| | | | 0.20 | 9.0 | 23.0 |
| Tapioca | 54.0[b] | 13% | 0.20 | 13.0 | 80.0 |
| Tapioca | 9.0[b] | 62% | 0.50 | 15.0 | 70.0 |
| Tapioca | 9.0[b,c,d] | 62% | 0.50 | 3.0 | 36.0 |

TABLE VII-continued

| | STARCH | | | | |
|---|---|---|---|---|---|
| | Funnel Viscosity (Seconds) | % Short Chain[e] Amylose | % Starch Solids | OPACITY % Transmittance | |
| | | | | Initial | 24 Hour |
| Control Fully branched Tapioca | — | — | 1.00 | 55.2 | 68.1 |

[b]Funnel viscosity in seconds at 10% solids and 22° C.
[c]Pre-retrogradation step used.
[d]Starch dispersion was homogenized.
[e]Percent short chain amylose was estimated from a standard curve.

EXAMPLE 8

This example illustrates that a variety of starches may be debranched.

The partial enzymatic debranching process of Example 1 was carried out on the following starches:

A. Corn starch debranched for 0, 1.0, 5.0 and 24.0 hours; and debranched to a 12 second (10% solids at 22° C. (72° F.)) funnel viscosity with 13 PUN of pullulanase/g starch;

B. Tapioca starch (21% solids) debranched for 0, 0.25, 1.0, 2.0 and 5.0 hours with 13 PUN of pullulanase/g starch; and C. Potato starch (18% solids) debranched for 0, 0.25, 1.0, 4.0 ad 16.0 hours with 13 PUN of pullulanase/g starch.

The funnel viscosity and percent short chain amylose were measured by the methods set forth above. Subjective observations of starch gelling characteristics were made. An acid-converted (32 WF) tapioca was also observed for comparative purposes. Results are set forth in Table VIII.

EXAMPLE 9

This example illustrates that a variety of partially debranched starch derivatives may be prepared by the process of this invention.

The derivatization reactions and the partial enzymatic debranching process were carried out as in Example 1 on the starches listed in Table IX.

Results are shown in Table IX. As the enzymatic debranching process progresses, the funnel viscosity of the starches decreases, indicating that derivatized and modified starches are suitable substrate for enzymatic debranching. Furthermore, waxy maize samples which were treated with 1% octenyl succinic anhydride, and partially, enzymatically debranched to 12 and 8.9 seconds, formed excellent clouds after pre-retrogradation.

EXAMPLE 10

This example illustrates the usefulness of fully debranched starches as opacifying agent in reduced-fat salad dressings.

A. Starch Debranching

Two types of starches were debranched: waxy maize starch and high amylose corn starch (Hylon VII starch, a 70% amylose corn starch obtained from National Starch and Chemical Company, Bridgewater, N.J.). A gelatinized starch dispersion was prepared according to the procedure of Example 1 except that the high amylose corn starch was jet-cooked at 154° C. (310° F.) and at 15% solids. The amount of pullulanase used was 7.5 ml and 7.0 ml per 100 g waxy maize and high amylose corn starch, respectively. The debranching of the waxy maize starch was allowed to proceed until a funnel viscosity of 8 seconds [at 19% solids and 22° C. (72° F.)] was reached and the starch was fully debranched. For high amylose corn starch, a reaction time of 48 hours was used to fully debranch the starch. After the reaction was completed, the enzyme was deactivated with acid and the product spray-dried. The opacity of the product in solution was measured by using a Brightimeter Micro S-5 (manufactured by Technidyne Corporation, New Albany, Ind., USA). A 1% starch solids dispersion was used to test opacity. Opacity was tested shortly after preparing the dispersions, and no stability tests were conducted.

Opacity test results are shown in Table VIII. The higher the Brightimeter value, the more opaque the starch appears. Results demonstrate the usefulness of a fully debranched starch as a temporary opacifier.

TABLE VIII

| OPACITY OF FULLY DEBRANCHED STARCH DISPERSION | |
|---|---|
| Waxy Maize - Control | 8.5 |
| Waxy Maize - Debranched | 7.0 |
| High Amylose Corn - Control | 14.0 |
| High Amylose Corn - Debranched | 20.0 |
| Blend (1:1) of Waxy Maize and High Amylose Control | 12.0 |
| Blend (1:1) of Waxy Maize and High Amylose Debranched | 22.0 |

B. Salad Dressing

The starch opacifiers were also incorporated into the no-fat salad dressing formulation set forth below.

| | CONTROL AND NON-FAT SALAD DRESSINGS FORMULATIONS | | |
|---|---|---|---|
| | Full-fat | No-Fat Experimental | |
| Ingredients | Control | Powder | Aqueous Paste |
| Soy Oil | 45% | 0% | 0% |
| THERMFLO Starch[a] | — | 6 | 6 |
| PURITY 420 Starch[b] | 3.4 | — | — |
| Opacifier[c] | — | 2 | — |
| 15% Opacifier Paste[d] | — | — | 13 |
| Water | 20.15 | 67.95 | 56.95 |
| White Vinegar | 17.2 | 14 | 14 |
| Sugar | 7.2 | 5 | 5 |
| Egg Yolk | 5 | — | — |
| Whey Protein Concentrate | — | 3 | .3 |
| Salt | 1.3 | 1.3 | 1.3 |
| Mustard Powder | 0.5 | 0.5 | 0.5 |
| TiO2 | — | 0.3 | — |
| Garlic | 0.025 | 0.025 | 0.025 |
| Onion | 0.025 | 0.025 | 0.025 |
| Citric Acid | 0.009 | 0.0091 | 0.0091 |
| Sodium Benzoate | 0.007 | 0.0079 | 0.0079 |
| Potassium Sorbate | 0.007 | 0.0079 | 0.0079 |
| Ca2Na2 EDTA | 0.007 | 0.0075 | 0.0075 |
| Paprika | 0.006 | 0.006 | 0.006 |
| | 100.0 | 100.0 | 100.0 |

[a]Modified waxy maize starch obtained from National Starch and Chemical Company, Bridgewater, New Jersey.
[b]Modified food starch obtained from National Starch and Chemical Company, Bridgewater, New Jersey.
[c]A fully debranched waxy maize starch and a fully debranched high amylose corn starch prepared by the method of Example 10, Part A, above, were tested in the no-fat experimental formulation.
[d]A paste of 15% solids starch opacifier (Example 10, Part A, above) in water.

Dry ingredients were blended, mixed with water and vinegar and held at 88° C. (190° F.) for 45 minutes. The mixture was cooled to room temperature and only lost volume was restored by the addition of water. Egg yolks were added to the control and mixed 3 minutes on a Hobart mixer at a #1 speed setting. The oil was slowly added to the control at a #2 speed setting and mixed for 3 minutes at a #3 speed setting. The opacifier power (or a 15% solids paste of opacifier starch in water) was added to the experimental sample and mixed for 3 minutes at a #2 speed setting. Samples were passed through a colloid mill (set at 200 holes) and refrigerated prior to evaluation.

The fat in the control formulation contributed much of the opacity of the dressing. Organoleptic (visual) evaluation of the salad dressings showed the suitability of using a fully debranched starch opacifier to replace fat in no-fat salad dressing applications.

| SALAD DRESSING EVALUATION | | |
|---|---|---|
| | Opacifier | Observation |
| Full-fat dressing (control) | Soy Oil Emulsion | Control |
| Dressing without Soy-Oil (control) | None | Not acceptable |
| Non-fat Dressing | Debranched Waxy Maize | Opacity similar to Full-fat Control |
| Non-fat Dressing | Debranched high amylose corn | Opacity similar to Full-fat Control |

EXAMPLE 11

This example illustrates the advantages of using debranched starches in a high temperature processed food, a canned retorted soup, to replace emulsified fat as the opacifier.

The high amylose corn starch opacifier of Example 10 was incorporated into the no-fat cream soup formulation, below.

| CREAM OF MUSHROOM SOUP CONTROL AND NO-FAT FORMULATIONS | | |
|---|---|---|
| Ingredients | No Fat (Experimental) | Full Fat (Control) |
| Soy Protein Concentrate | 0.31 | 0.31 |
| Sweet Whey | 0.72 | 0.72 |
| Whey/Ca Caseinate Blend | 0.26 | 0.26 |
| Heavy Whipping Cream | 0.00 | 1.06 |
| Vegetable Oil | 0.00 | 5.57 |
| Water (Soy) | 6.20 | 6.20 |
| Water (emulsion) | 16.52 | 15.89 |
| Starch Opacifier[a] | 6.00 | 0.00 |
| Maltrin 100 maltodextrin[b] | 0.00 | 0.00 |
| Mushroom (fresh) | 11.88 | 11.88 |
| Garlic | 0.01 | 0.01 |
| MSG (Accent ®) | 0.39 | 0.39 |
| Salt | 1.70 | 1.70 |
| Spices | 0.04 | 0.04 |
| Water (Mushrooms) | 13.54 | 13.54 |
| All-Purpose Flour | 5.17 | 5.17 |
| Purity W Starch[c] | 1.96 | 1.96 |
| Water | 14.26 | 14.26 |
| Water | 21.04 | 21.04 |
| | 100.00 | 100.00 |

[a]Starch opacifier was prepared by the method of Example 10, Part A.
[b]Maltrin 100 maltodextrin was obtained from Grain Processing Co., Muscatine, Iowa.
[c]Purity W starch, a modified food starch was obtained from National Starch and Chemical Company, Bridgewater, New Jersey.

The control soup was prepared by forming an emulsion of the soy protein, sweet whey, whey/calcium caseinate, heavy whipping cream, vegetable oil and water. The emulsion was combined with blanched mushrooms and spices. A thickener base was prepared by blending the remaining ingredients with water. This base was added to the emulsion mixture and cooked at 85° C. (185° F.). The mix was then canned in #1 size soup cans and retorted at 127° C. (260° F.) for ½ hour. The canned soup was then evaluated by opening the can, blending the retorted soup with three parts of water, and cooking to form a cream soup. The results of the organoleptic evaluation are shown below.

| MUSHROOM SOUP EVALUATION | | |
|---|---|---|
| Soup | Opacifier | Observation |
| Full-Fat (control) | cream/oil | control |
| No-Fat (control) | none | not acceptable |
| No-Fat (opacified) | fully debranched high amylose corn starch | similar to full fat control |

EXAMPLE 12

This example shows the usefulness of fully debranched starch as an opacifier in low-fat coffee creamer applications.

A debranched waxy maize starch was prepared according to the method of Example 10 except that 160 PUN of pullulanase per 100 g of starch was used and the starch was debranched to a funnel viscosity of 7.1 seconds (at 19% solids and 22° C.) and then spray-dried by the method of Example 1.

A blend of this fully debranched waxy maize starch and fully debranched high amylose corn starch (prepared according to Example 10) was prepared in a weight ratio of 1:1. A 15% solids dispersion of this blend in water was jet-cooked at 154° C. (310° F.), diluted to 10% solids and cooled rapidly under high agitation to about 4° C. (40° F.) where it was held without stirring for about 16 hours. An equal amount of 24 D.E. corn syrup solids (a starch/corn syrup blend of 1:1 on a dry basis) was added to the above dispersion and the dispersion was dried. The dried product showed good opacity in water.

The opacifier blend was incorporated into a low-fat non-dairy coffee creamer according to the formula below.

| COFFEE CREAMER FORMULATION | | |
|---|---|---|
| Ingredients | Experimental % | Control % |
| Soybean Fat | 5.0 | 21.6 |
| Distilled monoglyceride (Dimodan ®)[c] | 0.7 | 0.7 |
| Sodium stearoyl-2-lactylate (Artodan ®)[c] | 0.2 | 0.2 |
| Starch Emulsifier[a] | 2.5 | 2.5 |
| Opacifier Blend | 91.6 | 0.0 |
| Corn Syrup Solids[b] | — | 75.0 |
| | 100 | 100 |
| Water | 200 | 200 |

To prepare the coffee creamer, the monoglyceride and sodium stearoyl-2-lactylate were blended and melted together on low heat. The starch emulsifier and opacifier were added, followed by hot water with mixing. The mixture was homogenized using an Epenbach homogenizer on a high setting for 2 minutes. The resulting emulsion was checked for viscosity and microscopic particle size, then spray-dried.

The performance was evaluated in hot coffee. Results are shown below.

| COFFEE CREAMER EVALUATION | | | |
|---|---|---|---|
| Creamer | % Fat | % Opacifier Blend | Observation |
| Full-fat (control) | 22.5 | 0 | control |
| Low-fat creamer (control) | 5.0 | 0 | not acceptable |
| Low-fat creamer | 5.0 | 91.6 | similar to regular creamer |

Now that the preferred embodiments of the present invention have been described in detail, various modifications and improvements thereon will become readily apparent to those skilled in the art. Accordingly, the scope and spirit of the invention are to be limited only by the claims and not by the foregoing specification.

I claim:

1. A method for opacifying reduced-fat foods comprising formulating the reduced-fat food with an effective amount, up to 50%, by weight of the food, of a starch which starch has been fully debranched by treatment with an alpha-1,6-D-glucanohydrolase.

2. The method of claim wherein the starch is further modified by derivatization, conversion, or crosslinking or a combination thereof.

3. The method of claim 1, wherein the starch is selected from the group consisting essentially of waxy maize starch, corn starch, high amylose corn starch, tapioca starch, potato starch, wheat starch, rice starch and waxy rice starch.

4. The method of claim 1 wherein the reduced-fat food is formulated to mimic a full-fat food comprising an oil-in-water emulsion or a water-in-oil emulsion.

5. The method of claim 1, wherein the fully debranched starch is used to opacify a reduced-fat cream soup, in an amount up to 10% by weight, of the reduced-fat cream soup.

6. The method of claim 5, wherein the fully debranched starch is a high amylose corn starch and the cream soup is a retorted, canned soup.

7. The method of claim 4, wherein the fully debranched starch is used to opacify a reduced-fat salad dressing, in an amount up to 10% by weight, of the reduced-fat salad dressing.

8. The method of claim 7, wherein the fully debranched starch is a waxy maize starch or a high amylose corn starch, and the reduced-fat salad dressing is a pourable dressing or a spoonable dressing or a dry mix for reconstitution as a pourable dressing or a spoonable dressing.

9. The method of claim 8, wherein the reduced-fat salad dressing is a pourable dressing and the reduced fat salad dressing further comprises a stabilizer in an amount effective to prevent precipitation of the fully debranched starch from the reduced-fat salad dressing, up to 5%, by weight, of the reduced-fat salad dressing.

10. The method of claim 1, wherein the fully debranched starch is used to opacify a reduced-fat coffee creamer, in an amount up to 50%, by dry weight, of the reduced-fat coffee creamer.

11. The method of claim 10, wherein the fully debranched starch is a blend of debranched starches, comprising 30 to 70% of a fully debranched high amylose corn starch, which starch blend is dispersed in water, cooked to gelatinize the starch, debranched, blended with an inert carrier in a ratio of about 1:1, by weight, and spray-dried prior to formulating the reduced-fat coffee creamer.

12. A reduced-fat food, formulated with an effective amount, up to 50%, by weight, of a fully debranched starch, wherein the fully debranched starch is effective to render the reduced-fat food as opaque as a full-fat food equivalent.

13. A method for opacifying reduced-fat foods comprising formulating the reduced-fat food with an effective amount, from about 1 to 50%, by weight of the food, of a starch which starch has been partially debranched by treatment with an alpha-1,6-D-glucanohydrolase to yield at least 20%, by weight of the starch, short chain amylose.

14. The method of claim 13, wherein the starch is further modified by derivatization, conversion, or crosslinking or a combination thereof.

15. The method of claim 13, wherein the starch is selected from the group consisting essentially of waxy maize starch, corn starch, high amylose corn starch, tapioca starch, potato starch, wheat starch, rice starch and waxy rice starch.

16. The method of claim 13 wherein the reduced-fat food is formulated to mimic a full-fat food comprising an oil-in-water emulsion or a water-in-oil emulsion.

17. A reduced-fat food, formulated with an effective amount, from about 1 to 50%, by weight, of a partially debranched starch, wherein the partially debranched starch is effective to render the reduced-fat food as opaque as a full-fat equivalent.

* * * * *